(12) United States Patent
Watari

(10) Patent No.: US 11,185,299 B2
(45) Date of Patent: Nov. 30, 2021

(54) X-RAY FLUOROSCOPIC IMAGING APPARATUS

(71) Applicant: Shimadzu Corporation, Kyoto (JP)

(72) Inventor: Tomomi Watari, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 28 days.

(21) Appl. No.: 16/589,703

(22) Filed: Oct. 1, 2019

(65) Prior Publication Data

US 2020/0245959 A1 Aug. 6, 2020

(30) Foreign Application Priority Data

Feb. 1, 2019 (JP) .............................. JP2019-016777

(51) Int. Cl.
*A61B 6/00* (2006.01)
*A61B 6/04* (2006.01)

(52) U.S. Cl.
CPC .......... *A61B 6/4452* (2013.01); *A61B 6/0407* (2013.01); *A61B 6/467* (2013.01); *A61B 6/487* (2013.01)

(58) Field of Classification Search
CPC ..... A61B 6/4452; A61B 6/467; A61B 6/0407; A61B 6/487; A61B 6/06; A61B 6/0487
See application file for complete search history.

(56) References Cited

U.S. PATENT DOCUMENTS

| 7,177,393 | B2 * | 2/2007 | Kanemitsu | A61B 6/105 378/114 |
|---|---|---|---|---|
| 2013/0272499 | A1 * | 10/2013 | Simmons | A61B 6/487 378/62 |
| 2014/0321621 | A1 * | 10/2014 | Lee | H05G 1/02 378/197 |
| 2015/0313561 | A1 * | 11/2015 | Kwak | A61B 6/4482 378/197 |
| 2017/0025761 | A1 * | 1/2017 | Kim | H01Q 21/00 |
| 2018/0116524 | A1 * | 5/2018 | Aoshima | A61B 6/4064 |
| 2018/0116623 | A1 * | 5/2018 | Inoue | H05G 1/64 |
| 2018/0199909 | A1 * | 7/2018 | Kim | G21K 4/00 |
| 2020/0029922 | A1 * | 1/2020 | Boehm | A61B 6/547 |

FOREIGN PATENT DOCUMENTS

JP 2000-166905 A 6/2000

* cited by examiner

*Primary Examiner* — Marcus H Taningco
(74) *Attorney, Agent, or Firm* — Muir Patent Law, PLLC

(57) ABSTRACT

An X-ray fluoroscopic imaging apparatus includes an imaging system, a gripping portion, and an operation panel portion. The gripping portion extends along a direction substantially parallel to the operation panel portion, and is connected to the operation panel portion. The plurality of operation input portions includes at least an X-ray irradiation range adjustment portion for adjusting an X-ray irradiation range. The X-ray irradiation range adjustment portion is provided at a position on a side of the gripping portion in a plane of the operation panel portion.

9 Claims, 9 Drawing Sheets

X-RAY FLUOROSCOPIC IMAGING APPARATUS

CROSS-REFERENCE TO RELATED APPLICATIONS

The priority application number JP2019-016777, entitled "X-ray fluoroscopic imaging apparatus", filed on Feb. 1, 2019, and invented by Tomomi Watari, upon which this patent application is based, is hereby incorporated by reference.

BACKGROUND OF THE INVENTION

Field of the Invention

The present invention relates to an X-ray fluoroscopic imaging apparatus, and more particularly to an X-ray fluoroscopic imaging apparatus for imaging while moving an imaging system by an operator.

Description of the Background Art

Conventionally, an X-ray fluoroscopic imaging apparatus for imaging while moving an imaging system by an operator is known. Such an X-ray fluoroscopic imaging apparatus is disclosed in, for example, Japanese Unexamined Patent Application Publication No. 2000-166905.

In Japanese Unexamined Patent Application Publication No. 2000-166905, an X-ray fluoroscopic imaging table is disclosed in which a top board configured to place a subject thereon, and an imaging system including a control panel, a quick imaging device, an image intensifier, and a television camera are provided. The control panel of the X-ray fluoroscopic imaging table disclosed in Japanese Unexamined Patent Application Publication No. 2000-166905 is provided with an imaging system operation handle and an imaging switch. In the X-ray fluoroscopic imaging apparatus disclosed in Japanese Unexamined Patent Application Publication No. 2000-166905, when the operation switch is pressed, X-rays are emitted toward the subject to image blood flows of blood vessels contrasted by a contrast agent administered to the subject.

In the X-ray fluoroscopic imaging table described in Japanese Unexamined Patent Application Publication No. 2000-166905, it is configured to be able to move the imaging system by manipulating the imaging system operation handle by an operator. Further, in Japanese Unexamined Patent Application Publication No. 2000-166905, the operator moves the imaging system while pressing the imaging switch to image the blood flow while operating so that the blood flow of the subject is always reflected on the TV monitor.

Here, as disclosed in Japanese Unexamined Patent Application Publication No. 2000-166905, in order to perform imaging while moving the imaging system so that the blood flow of the subject is always reflected on the TV monitor, it is conceivable that the operator moves the imaging system by gripping the imaging system operation handle while confirming the blood flow (imaging range) in the fluoroscopic image reflected on the TV monitor. Although not disclosed in Japanese Unexamined Patent Application Publication No. 2000-166905, when the imaging position is changed, it is preferable to also adjust the irradiation range of X-rays in accordance with the region (region of interest) desired to be imaged. Further, in order to repeatedly perform the movement of the imaging system and the adjustment of the X-ray irradiation range, it is preferably configured to be able to adjust the X-ray irradiation range in a state in which the operator grips the gripping portion.

In such a case, if the operability of adjusting the X-ray irradiation range in a state in which the operator grips the gripping portion is poor, imaging cannot be performed efficiently, so that the imaging time becomes long. If the imaging time becomes long, it will be a burden on the operator and the subject. Under the circumstance, an X-ray fluoroscopic imaging apparatus capable of efficiently adjusting the X-ray irradiation range is desired.

The present invention has been made to solve the aforementioned problems, and one object of the present invention is to provide an X-ray fluoroscopic imaging apparatus capable of efficiently adjusting an X-ray irradiation range in a state in which an operator grips a gripping portion.

SUMMARY OF THE INVENTION

In order to attain the above-described object, the X-ray fluoroscopic imaging apparatus according to one aspect of the present invention includes:
  a top board configured to place a subject thereon;
  an imaging system including an X-ray source configured to emit X-rays toward the subject and a detector configured to detect X-rays emitted from the X-ray source and transmitted through the subject;
  a gripping portion configured to be gripped by an operator when the operator moves the imaging system; and
  an operation panel portion provided integrally to the imaging system and provided with a plurality of operation input portions each for receiving an operation input for operating the imaging system,
  wherein the gripping portion extends along a direction substantially parallel to the operation panel portion, and is connected to the operation panel portion,
  wherein the plurality of operation input portions includes at least an X-ray irradiation range adjustment portion for adjusting an X-ray irradiation range, and
  wherein the X-ray irradiation range adjustment portion is provided at a position on a side of the gripping portion in a plane of the operation panel portion.

As described above, the X-ray fluoroscopic imaging apparatus according to one aspect of the present invention includes the X-ray irradiation range adjustment portion provided at the position on the side of the gripping portion in the plane of the operation panel portion. This makes it possible to arrange the X-ray irradiation range adjustment portion close to the gripping portion, so that it is possible to operate the X-ray irradiation range adjustment portion in a state in which the operator grips the gripping portion. As a result, it is possible to efficiently adjust the X-ray irradiation range in a state in which the operator grips the gripping portion.

In the X-ray fluoroscopic imaging apparatus according to the aforementioned one aspect of the present invention, preferably, the plurality of operation input portions further includes a relative position adjustment portion configured to receive an input for adjusting a relative position of the top board and the imaging system, and not only the X-ray irradiation range adjustment portion but also the relative position adjustment portion are provided at positions on the side of the gripping portion in the plane of the operation panel portion.

By configuring as described above, it is possible to perform not only the adjustment of the X-ray irradiation range but also the adjustment of the relative position of the top board and the imaging system in a state in which the gripping portion is gripped. As a result, the adjustment of the X-ray irradiation range and the adjustment of the relative position of the top board and the imaging system can be efficiently performed without visually recognizing the operation panel portion.

In this case, preferably, the plurality of operation input portions is arranged in a plurality of rows in a direction intersecting with the gripping portion in the plane of the operation panel portion, and the X-ray irradiation range adjustment portion and the relative position adjustment portion are arranged in a row closest to the side of the gripping portion among the plurality of rows in which the plurality of operation input portions are arranged.

By configuring as described above, the X-ray irradiation range adjustment portion and the relative position adjustment portion can be arranged closer to the gripping portion than the other operation input portions. As a result, the X-ray irradiation range adjustment portion and the relative position adjustment portion can be easily operated in a state in which the gripping portion is gripped. Therefore, the adjustment of the X-ray irradiation range and the adjustment of the relative position of the top board and the imaging system can be performed more efficiently.

In the configuration in which the X-ray irradiation range adjustment portion and the relative position adjustment portion are arranged in the row closest to the side of the gripping portion, preferably, the row in which the X-ray irradiation range adjustment portion and the relative position adjustment portion are arranged is a row located at a position closest to a connecting portion of the gripping portion with respect to the operation panel portion among the plurality of rows in which the plurality of operation input portions is arranged in the plane of the operation panel portion.

By configuring as described above, the X-ray irradiation range adjustment portion and the relative position adjustment portion can be arranged at a position much more closer to the gripping portion than the other operation input portions. As a result, the X-ray irradiation range adjustment portion and the relative position adjustment portion can be easily operated in a state in which the gripping portion is gripped. Therefore, the adjustment of the X-ray irradiation range and the adjustment of the relative position of the top board and the imaging system can be performed even more efficiently.

In the configuration in which the X-ray irradiation range adjustment portion and the relative position adjustment portion are arranged in the row closest to the side of the gripping portion, preferably, the operation panel portion is provided with a cutout portion, the gripping portion is provided so as to connect opposing inner surfaces of the cutout portion on a side of an open end portion of the cutout portion, and the X-ray irradiation range adjustment portion and the relative position adjustment portion are respectively provided at positions corresponding to corner portions of the cutout portion in the plane of the operation panel portion.

By configuring as described above, unlike the configuration in which a U-shaped gripping portion is attached to the side surface of the operation panel portion that does not have a cutout portions, it is possible to prevent the gripping portion from protruding from the side surface of the operation panel portion. As a result, it is possible to prevent other devices or the operator from colliding with the gripping portion. Also, in comparison with the configuration in which the X-ray irradiation range adjustment portion and the relative position adjustment portion are provided on the side of the open end portion of the cutout portion, the gripping portion, the X-ray irradiation range adjustment portion, and the relative position adjustment portion can be arranged in positions apart from each other to some extent. Therefore, in a state in which the user grips the gripping portion, it is possible to arrange the X-ray irradiation range adjustment portion and the relative position adjustment portion at positions (distance) which can be easily operated by a forefinger (second finger) which is the most dexterous finger among human fingers. As a result, the X-ray irradiation range adjustment portion and the relative position adjustment portion can be arranged at positions which are close to the gripping portion and easily operable with a forefinger.

In the configuration in which the X-ray irradiation range adjustment portion and the relative position adjustment portion are arranged in the row closest to the gripping portion, preferably, the operation panel portion is provided with a cutout portion, the gripping portion is provided so as to connect opposing inner surfaces of the cutout portion on a side of an open end portion of the cutout portion, and the X-ray irradiation range adjustment portion and the relative position adjustment portion are respectively provided at positions opposite to the side of the open end portion of the cutout portion where the gripping portion is provided in the plane of the operation panel portion.

Even by configuring as described above, in the same manner as the configuration in which the X-ray irradiation range adjustment portion and the relative position adjustment portion are respectively provided at positions corresponding to the corner portions of the cutout portion in the plane of the operation panel portion, the X-ray irradiation range adjustment portion and the relative position adjustment portion can be arranged at positions which are close to the gripping portion and easily operable with a forefinger.

In the configuration in which the X-ray irradiation range adjustment portion and the relative position adjustment portion are provided at positions on the side of the gripping portion in the plane of the operation panel portion, preferably, the X-ray irradiation range adjustment portion and the relative position adjustment portion are each configured to be larger in size than other operation input portions in a direction of protruding from a surface of the operation panel portion.

By configuring as described above, since the X-ray irradiation range adjustment portion and the relative position adjustment portion protrude from the surface of the operation panel portion, it is possible to access the X-ray irradiation range adjustment and the relative position adjustment portion naturally without visually recognizing them by simply moving a finger above the operation panel portion surface. Therefore, the X-ray irradiation range and the relative position of the top board can be adjusted without visually recognizing the operation panel portion. As a result, the operability at the time of adjusting the X-ray irradiation range and the relative position of the top board can be further improved.

In the configuration in which the X-ray irradiation range adjustment portion and the relative position adjustment portion are provided at positions on the side of the gripping portion in the plane of the operation panel portion, preferably, the X-ray irradiation range adjustment portion and the relative position adjustment portion are each provided with a placement portion on which a finger of the operator is placed and a shaft portion, and configured to be movable in a radial direction centering on the shaft portion in a state in which the finger is placed on the placement portion, and further configured to accept an input for adjusting the X-ray radiation range and an input for adjusting the relative position of the top board and the imaging system, based on a movement direction of the shaft portion.

By configuring as described above, by moving the center of gravity of the placement portion in a state in which a finger is placed on the placement portion, the X-ray irradiation range adjustment portion and the relative position adjustment portion can be moved. Therefore, as compared with the configuration in which the adjustment of the radiation range of the X-ray and the adjustment of the relative position of the top board are performed using an input portion corresponding to each direction, such as, e.g., arrow keys, it is possible to intuitively operate the X-ray irradiation range adjustment portion and the relative position adjustment portion. As a result, even in the case of operating the X-ray irradiation range adjustment portion and the relative position adjustment portion without visually recognizing the operation panel portion, it is possible to easily adjust the X-ray irradiation range and the top board relative position.

In the configuration in which the X-ray irradiation range adjustment portion and the relative position adjustment portion are provided at positions on the side of the gripping portion in the plane of the operation panel portion, preferably, the X-ray irradiation range adjustment portion and the relative position adjustment portion are respectively provided on both sides in a direction in which the gripping portion extends centering on the gripping portion in the operation panel portion.

By configuring as described above, since the X-ray irradiation range adjustment portion and the relative position adjustment portion are provided on both sides in the extending direction of the gripping portion centering on the gripping portion, even if the user grips the gripping portion with either hand, in a state in which the gripping portion is gripped, it is possible to manipulate the X-ray irradiation range adjustment portion and the relative position adjustment portion. Therefore, as compared with the configuration in which the X-ray irradiation range adjustment portion and the relative position adjustment portion are provided on only one side of the operation panel portion, the operability of the X-ray irradiation range adjustment portion and the relative position adjustment portion can be improved. As a result, the usability of the user can be improved.

DESCRIPTION OF PREFERRED EMBODIMENTS

Hereinafter, embodiments embodying the present invention will be described with reference to the drawings.

A configuration of an X-ray fluoroscopic imaging apparatus 100 according to one embodiment will be described with reference to FIG. 1 to FIG. 11.

(Configuration of X-Ray Fluoroscopic Imaging Apparatus)

Figure 1:
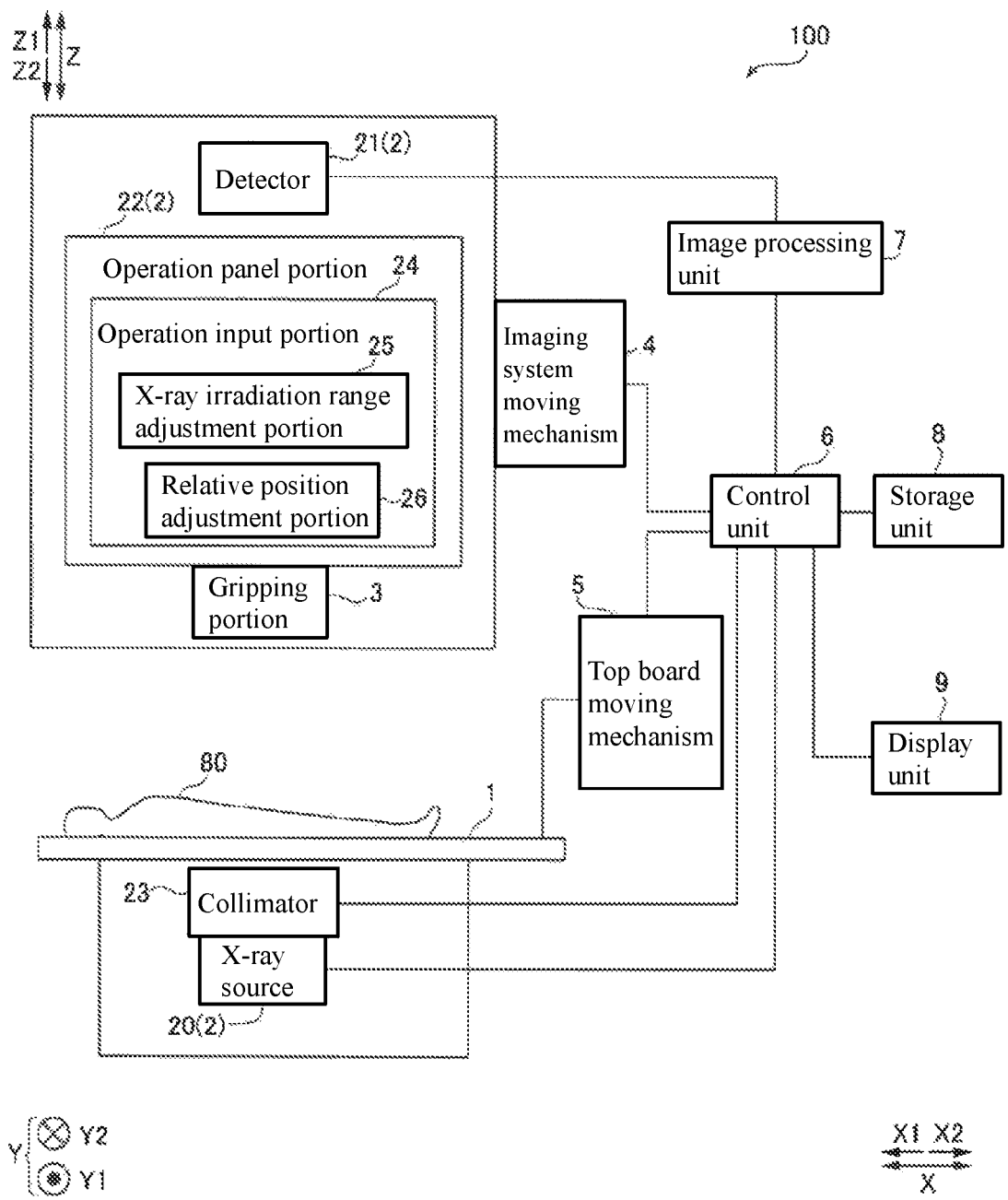
FIG. 1 is a block diagram showing an overall configuration of an X-ray fluoroscopic imaging apparatus according to one embodiment.

As shown in FIG. 1, the X-ray fluoroscopic imaging apparatus 100 of this embodiment is provided with a top board 1, an imaging system 2, a gripping portion 3, an imaging system moving mechanism 4, a top board moving mechanism 5, a control unit 6, an image processing unit 7, and a storage unit 8. Further, in the example shown in FIG. 1, the control unit 6 of the X-ray fluoroscopic imaging apparatus 100 is connected to a display unit 9.

The top board 1 is configured to place a subject 80 thereon. The top board 1 is formed in a rectangular flat plate shape in plan view. The subject 80 is placed on the top board 1 so that the head-to-foot direction of the subject 80 is in parallel to a direction along the long side of the rectangle and the left-right direction of the subject P is along the short side of the rectangle.

In this specification, the vertical direction is defined as the Z-direction, the upper direction is defined as the Z1-direction, and the lower direction is defined as the Z2-direction. Two directions orthogonal to each other in the horizontal direction are defined as an X-direction and a Y-direction. One of the X-directions is defined as an X1-direction and the other is defined as an X2-direction. One of the Y-directions is defined as a Y1-direction and the other is defined as a Y2-direction. In the example shown in FIG. 1, the subject 80 is placed such that the head of the subject 80 faces in the X1-direction. Further, the head-to-foot direction of the subject 80 is a direction along a straight line connecting the head and the foot of the subject 80. That is, the X-direction is the longitudinal direction of the top board 1. On the other hand, the Y-direction is the short direction of the top board 1.

The imaging system 2 includes an X-ray source 20, a detector 21, and an operation panel portion 22. The imaging system 2 is configured to capture an X-ray fluoroscopic image by detecting the X-rays emitted from the X-ray source 20 to the subject 80 using the detector 21. The X-ray source 20 is configured to emit X-rays toward the subject 80 when a voltage is applied by an X-ray tube drive unit (not shown). Further, the X-ray source 20 is provided on the Z2-direction side. The detector 21 is provided on the Z1-direction side. That is, the X-ray source 20 and the detector 21 are provided at mutually opposing positions across the top board 1. Further, the X-ray source 20 is provided with a collimator 23 capable of adjusting the X-ray radiation field, which is the X-ray irradiation range 70 (see FIG. 10).

The collimator 23 is arranged between the X-ray source 20 and the detector 21. The collimator 23 is configured to be able to shield X-rays. The collimator 23 is configured to be able to adjust the X-ray irradiation range 70 by partially shielding the X-rays emitted from the X-ray source 20. The collimator 23 contains heavy metals, such as, e.g., lead, gold, and tungsten.

The detector 21 is configured to detect X-rays emitted from the X-ray source 20 and transmitted through the subject 80. The detector 21 includes, for example, an FPD (Flat Panel Detector) or an II (Image Intensifier). The detector 21 is composed of a plurality of conversion elements (not shown) and a plurality of pixel electrodes (not shown) arranged on the plurality of conversion elements. The plurality of conversion elements and the pixel electrodes are arranged in an array on the detection surface at a predetermined cycle (pixel pitch). Further, the detector 21 is configured to output the acquired image signal to the image processing unit 7.

The gripping portion 3 is gripped when the operator 81 (see FIG. 4) moves the imaging system 2. That is, the operator 81 moves the imaging system 2 by applying a force in the direction in which the imaging system 2 is to be moved in the state in which the gripping portion 3 is gripped. The gripping portion 3 extends along a direction (X-direction) substantially parallel to the operation panel portion 22, and is attached to the operation panel portion 22. The gripping portion 3 is made of, for example, resin. In this embodiment, the operator 81 is, for example, a doctor or a technician.

The operation panel portion 22 is integrally provided in the imaging system 2. Further, the operation panel portion 22 is provided with a plurality of operation input portions 24 for receiving an operation input for operating the imaging system 2. The plurality of operation input portions includes at least an X-ray irradiation range adjustment portion 25 for adjusting an X-ray irradiation range 70. The detailed configuration of the X-ray irradiation range adjustment portion 25 will be described later.

The imaging system moving mechanism 4 movably holds the imaging system 2. The imaging system moving mechanism 4 is configured to move the imaging system 2 in the direction of the force applied by the operator 81 to the gripping portion 3 under the control of the control unit 6. The imaging system moving mechanism 4 functions as a power assist mechanism, for example, when moving the imaging system 2 by the operator 81. Further, when the imaging system 2 is operated (remotely controlled) by the operation input portion 24 or a console (not shown) provided at a position different from the X-ray fluoroscopic imaging apparatus 100, the imaging system moving mechanism 4 functions as a moving mechanism for moving the imaging system 2 based on the input signal from the operation input portion 24 or the control of the control unit (not shown) of the console. The imaging system moving mechanism 4 includes an X-direction linear motion mechanism 41 (see FIG. 3), a Y-direction linear motion mechanism 42 (see FIG. 3), and a Z-direction linear motion mechanism 43 (see FIG. 3). The detailed configuration of the imaging system moving mechanism 4 will be described later.

The top board moving mechanism 5 is configured to move so as to change the relative position of the top board 1 with respect to the imaging system 2 under the control of the control unit 6. Specifically, the top board moving mechanism 5 is configured to be able to change the relative position of the top board 1 and the imaging system 2 by moving the top board 1 in the X-direction and the Y-direction. The top board moving mechanism 5 includes an X-direction linear motion mechanism 50 and a Y-direction linear motion mechanism 51. The detailed configuration of the top board moving mechanism 5 will be described later.

The control unit 6 is configured to control the imaging system moving mechanism 4 to perform the power assist when the operator 81 moves the imaging system 2. The control unit 6 is configured to control the top board moving mechanism 5 to relatively move the top board 1 and the imaging system 2. Further, the control unit 6 is configured to control the collimator 23 to adjust the X-ray irradiation range 70. The control unit 6 is a computer configured so as to include a CPU (Central Processing Unit), a ROM (Read Only Memory), a RAM (Random Access Memory), and the like.

The image processing unit 7 is configured to generate an X-ray fluoroscopic image based on the image information acquired by the imaging system 2. Specifically, the image processing unit 7 is configured to generate an X-ray fluoroscopic image as a moving image. The X-ray fluoroscopic image generated by the image processing unit 7 is displayed on the display unit 9. Therefore, the operator 81 can change the imaging position and/or change the X-ray irradiation range 70 in real time while confirming the X-ray fluoroscopic image generated by the image processing unit 7. The image processing unit 7 includes a processor, such as, e.g., a GPU (Graphics Processing Unit) and an FPGA (Field-Programmable Gate Array) configured for image processing.

The display unit 9 is configured as, for example, a liquid crystal display. The display unit 9 is configured to display the X-ray fluoroscopic image generated by the image processing unit 7 based on the image information imaged by the imaging system 2.

The storage unit 8 includes, for example, an HDD (hard disk drive) or a nonvolatile memory. The storage unit 8 is configured to be able to store the image information captured by the imaging system 2, an X-ray fluoroscopic image generated by the image processing unit 7, and the like.

Figure 2:
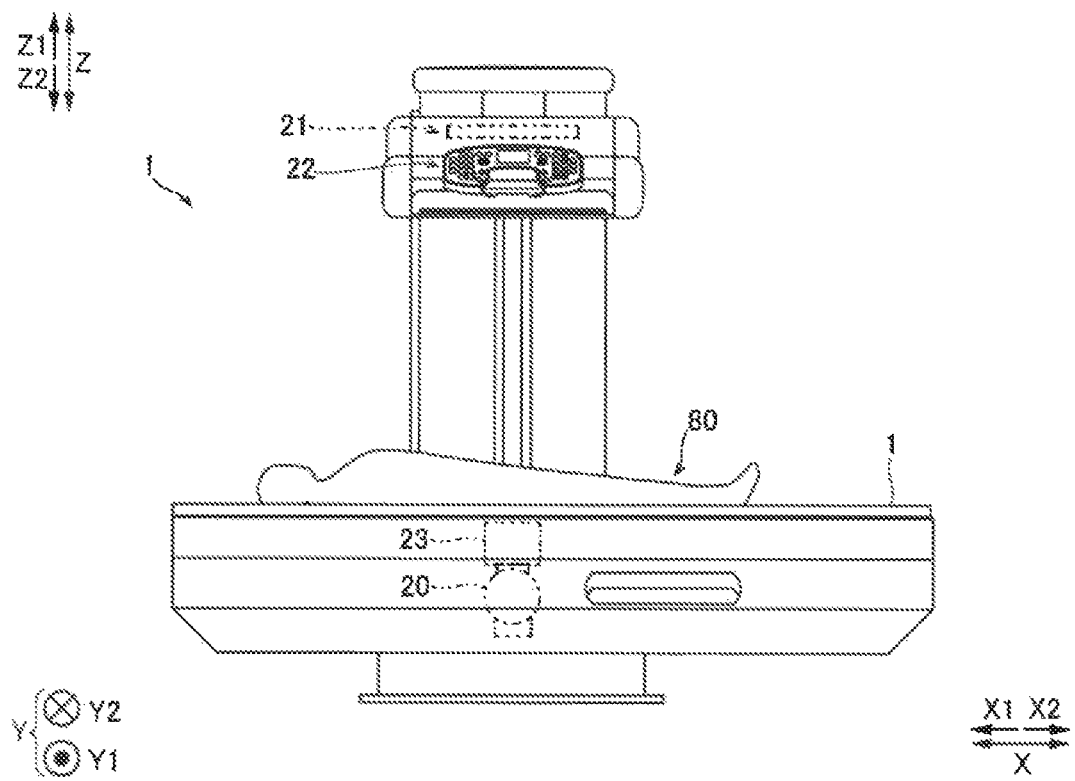
FIG. 2 is a schematic diagram of an X-ray fluoroscopic imaging apparatus according to one embodiment as viewed from the Y-direction.

As shown in FIG. 2, the X-ray fluoroscopic imaging apparatus 100 captures an X-ray fluoroscopic image in a state in which the subject 80 is placed on the top board 1. The operator 81 can capture an X-ray fluoroscopic image of a region (region of interest) to be confirmed by performing imaging while moving the imaging system 2.

(Imaging System Moving Mechanism and Top Board Moving Mechanism)

Next, with reference to FIG. 3, the configurations of the imaging system moving mechanism 4 and the top board moving mechanism 5 will be described.

Figure 3:
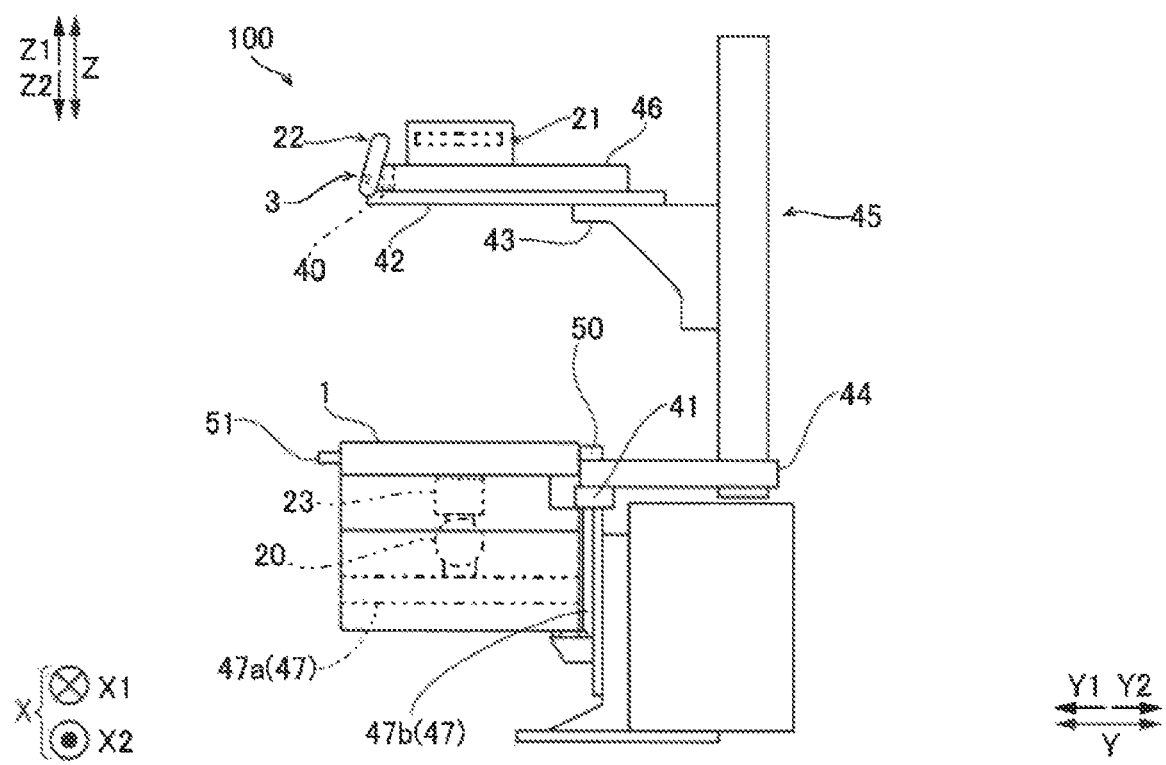
FIG. 3 is a schematic diagram of an X-ray fluoroscopic imaging apparatus according to one embodiment as viewed in the X-direction.

As shown in FIG. 3, the imaging system moving mechanism 4 includes a force detection unit 40, an X-direction linear motion mechanism 41, a Y-direction linear motion mechanism 42, a Z-direction linear motion mechanism 43, a base portion 44, a support post 45, an imaging system holding portion 46, and an X-ray source holding portion 47.

The force detection unit 40 detects the direction of the force applied to the operation panel portion 22. Specifically, the force detection unit 40 is configured to detect each of the horizontal and vertical translation direction (X, Y, Z-direction) forces applied to the gripping portion 3.

The base portion 44 is attached to the X-direction linear motion mechanism 41. In addition, the base portion 44 is attached to a support post 45. The support post 45 is provided with a Z-direction linear motion mechanism 43. The support post 45 holds a Y-direction linear motion mechanism 42 via the Z-direction linear motion mechanism 43. The Y-direction linear motion mechanism 42 holds an imaging system holding portion 46. The imaging system holding portion 46 holds an operation panel portion 22 and a detector 21. Further, as shown in FIG. 3, the operation panel portion 22 is held by the imaging system holding portion 46 in a state of being inclined with respect to the vertical direction (Z-direction).

The X-direction linear motion mechanism 41 is, for example, a belt-pulley mechanism including a drive motor (not shown), a pair of rollers (not shown), and a timing belt (not shown). The X-direction linear motion mechanism 41 is configured to extend along the X-direction, and the base portion 44 is configured to be movable in the X-direction. That is, the imaging system moving mechanism 4 is configured to be able to move the base portion 44 in the X-direction based on the force in the X-direction that the operator 81 applies to the gripping portion 3.

The Z-direction linear motion mechanism 43 is, for example, a belt-pulley mechanism including a drive motor (not shown), a pair of rollers (not shown), and a timing belt (not shown). The Z-direction linear motion mechanism 43 is configured to be able to move the imaging system holding portion 46 in the Z-direction by moving in the Z-direction along the support post 45. That is, the imaging system moving mechanism 4 is configured to be able to move the base portion 44 in the Z-direction based on the force in the Z-direction that the operator 81 applies to the gripping portion 3.

The Y-direction linear motion mechanism 42 is, for example, a belt-pulley mechanism including a drive motor (not shown), a pair of rollers (not shown), and a timing belt (not shown). The Y-direction linear motion mechanism 42 is configured to be able to move the operation panel portion 22 and the detector 21 in the Y-direction. That is, the imaging system moving mechanism 4 is configured to be able to move the operation panel portion 22 and the detector 21 in the Y-direction based on the force in the Y-direction that the operator 81 applied to the gripping portion 3.

The X-ray source holding portion 47 holds the X-ray source 20. The X-ray source holding portion 47 includes a holding portion 47a and a connecting portion 47b. The holding portion 47a holds the X-ray source 20. The connecting portion 47b connects the base portion 44 and the holding portion 47a. That is, the X-ray source 20 is connected to the base portion 44 via the holding portion 47a and the connecting portion 47b. Therefore, the X-ray source 20 is configured to move integrally with the imaging system 2 as the imaging system 2 moves.

The top board moving mechanism 5 includes an X-direction linear motion mechanism 50 extending in the X-direction and a Y-direction linear motion mechanism 51 extending in the Y-direction. The X-direction linear motion mechanism 50 is, for example, a belt-pulley mechanism including a drive motor (not shown), a pair of rollers (not shown), and a timing belt (not shown). The X-direction linear motion mechanism 50 is configured to be able to move the top board 1 in the X-direction based on the input of the relative position adjustment portion 26. The Y-direction linear motion mechanism 51 is, for example, a belt-pulley mechanism including a drive motor (not shown), a pair of rollers (not shown), and a timing belt (not shown). The Y-direction linear motion mechanism 51 is configured to be able to move the top board 1 in the Y-direction based on the input of the relative position adjustment portion 26.

(Adjustment of Imaging System when Imaging)

Figure 4:
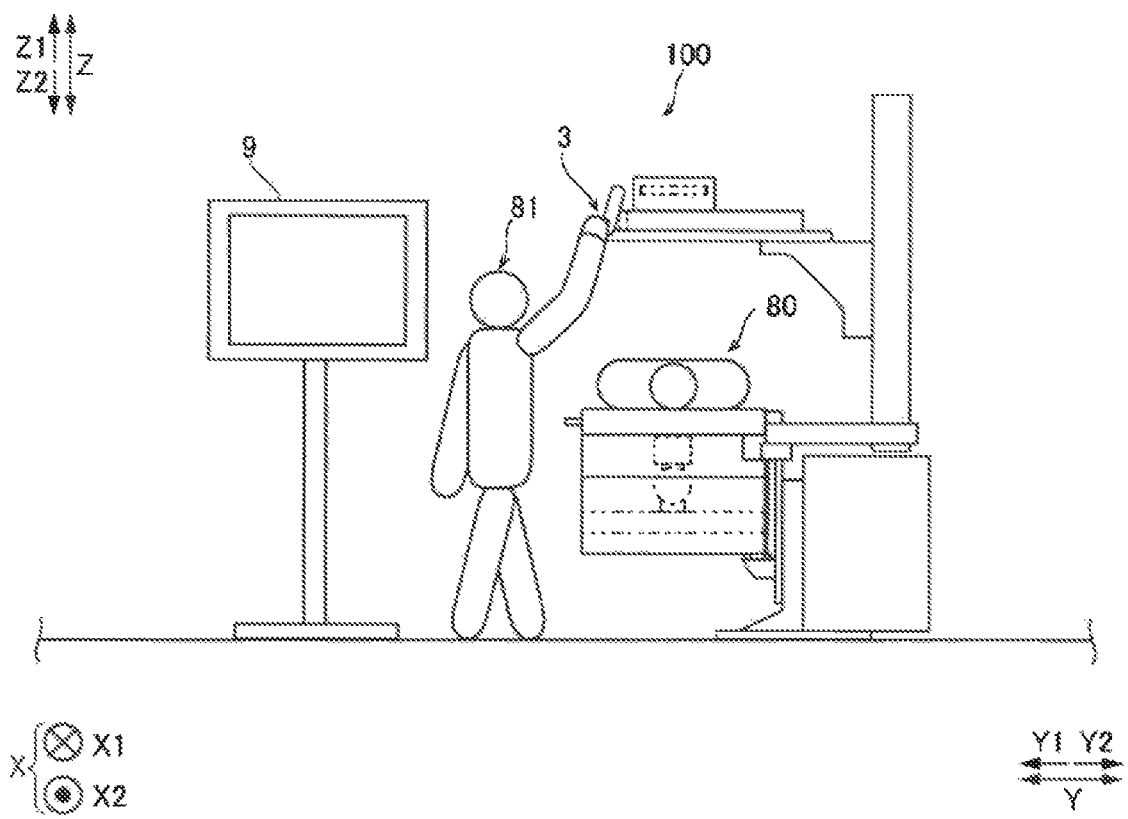
FIG. 4 is a schematic diagram for explaining a position adjustment of an imaging system when capturing an X-ray fluoroscopic image by an X-ray fluoroscopic imaging apparatus according to one embodiment.

As shown in FIG. 4, when capturing the X-ray fluoroscopic image, the operator 81 moves the imaging system 2 and adjusts the X-ray irradiation range 70 in a state in which the subject 80 is placed on the top board 1. Specifically, the operator 81 performs the imaging of the subject 80 while moving the imaging system 2 in a state of gripping the gripping portion 3. Also, the adjustment of the X-ray irradiation range 70 is performed so as to be in a range suitable for the region of interest as the imaging system 2 moves. The movement of the imaging system 2 and the adjustment of the X-ray irradiation range 70 are performed while the operator 81 is looking at the X-ray fluoroscopic image displayed on the display unit 9. The operator 81 repeats the movement of the imaging system 2, the adjustment of the X-ray irradiation range 70 and the image capturing to thereby image a predetermined region of interest.

The operator 81 moves the imaging system 2 and adjusts the X-ray irradiation range 70 while watching the X-ray fluoroscopic image displayed on the display unit 9. Therefore, it is configured such that the operator 81 can move the imaging system 2 by applying a force in a direction desired to be moved while gripping the gripping portion 3 provided to the operation panel portion 22. Further, the operation panel portion 22 is provided with an X-ray irradiation range adjustment portion 25 and is configured to be able to adjust the X-ray irradiation range 70 by operating the X-ray irradiation range adjustment portion 25.

(Operation Panel Portion)

Figure 5:
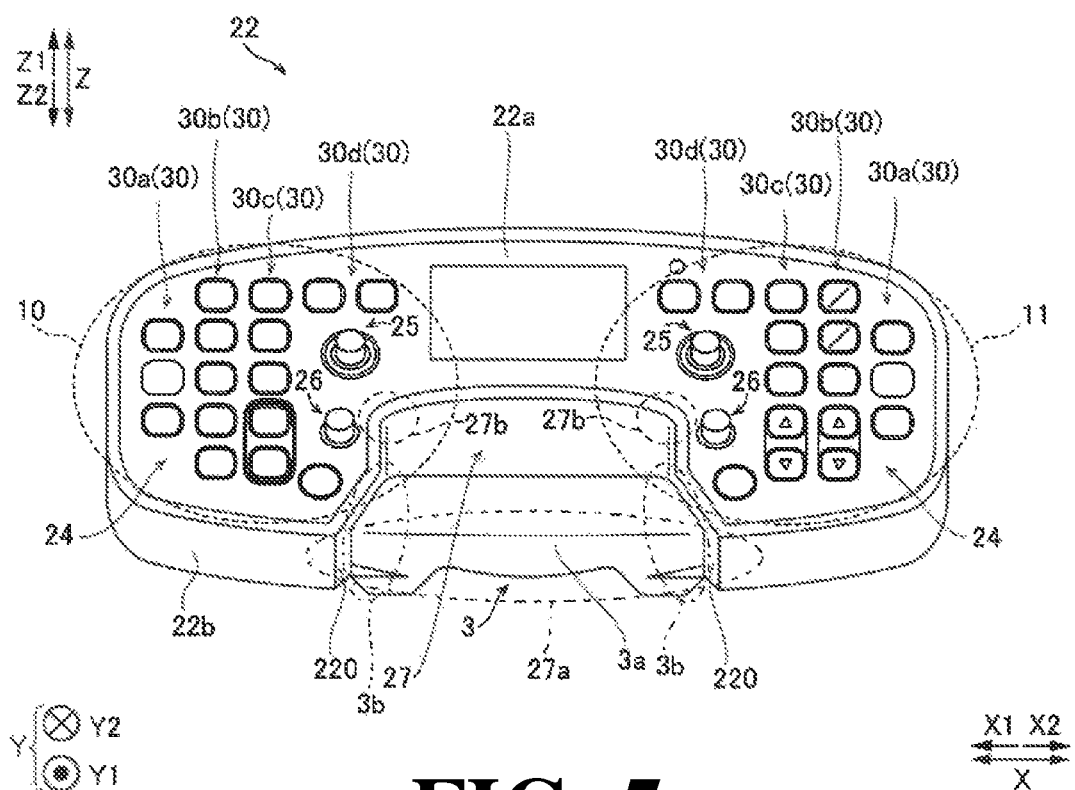
FIG. 5 is a schematic diagram of an operation panel portion of an X-ray fluoroscopic imaging apparatus according to one embodiment.

Specifically, as shown in FIG. 5, the operation panel portion 22 includes a panel portion 22a and a housing 22b. The panel portion 22a is held by the imaging system moving mechanism 4 (imaging system holding portion 46) via the housing 22b. The panel portion 22a has a rectangular shape in plan view. In the example shown in FIG. 5, the panel portion 22a has a rectangular shape with rounded corners. The operation panel portion 22 is provided with a plurality of operation input portions 24 for receiving an operation input for operating the imaging system 2. The plurality of operation input portions 24 is used by the operator 81 to perform input operations at the time of imaging. In this embodiment, the plurality of operation input portions 24 includes at least an X-ray irradiation range adjustment portion 25 for adjusting an X-ray irradiation range 70. The X-ray irradiation range adjustment portion 25 is provided at a position on the side of the gripping portion 3 in the plane of the operation panel portion 22. The plurality of operation input portions 24 includes a relative position adjustment portion 26 configured to receive an input for adjusting the relative position of the top board 1 and the imaging system 2. As shown in FIG. 5, not only the X-ray irradiation range adjustment portion 25 but also the relative position adjustment portion 26 are provided at positions on the side of the gripping portion 3 in the plane of the operation panel portion 22.

In this embodiment, the plurality of operation input portions 24 are arranged in a plurality of rows in a direction intersecting with the gripping portion 3 in the plane of the operation panel portion 22. In this embodiment, for example, the plurality of operation input portions 24 is arranged from the outside in four rows in the order of the row 30a, the row 30b, the row 30c, and the row 30d. Further, the X-ray irradiation range adjustment portion 25 and the relative position adjustment portion 26 are arranged in a row 30d closest to the side of the gripping portion 3 among the plurality of rows 30 in which the plurality of operation input portions is arranged. Further, the row 30d in which the X-ray irradiation range adjustment portion 25 and the relative position adjustment portion 26 are arranged is a row 30d located at a position closest to the connecting portion 3b of the gripping portion 3 with respect to the operation panel portion 22 among the plurality of rows 30 in which the plurality of operation input portions 24 is arranged in the plane of the operation panel portion 22.

As shown in FIG. 5, the gripping portion 3 includes a main body portion 3a to be gripped by the operator 81 and a connecting portion 3b connected to the operation panel portion 22. The connecting portion 3b is provided on both sides of the main body portion 3a in the extending direction of the gripping portion 3. Further, the panel portion 22a has a cutout portion 27. In the example shown in FIG. 5, the panel portion 22a has a cutout portion 27 at a position substantially in the center in the X-direction and on the Z2-direction side. The cutout portion 27 has a U-shape in plan view. The cutout portion 27 has an open end portion 27a and a corner portions 27b.

The gripping portion 3 is provided to the housing 22b. Specifically, the gripping portion 3 is provided so as to connect facing inner surfaces 220 of the cutout portion 27 on the side of the open end portion 27a of the cutout portion 27. The X-ray irradiation range adjustment portion 25 and the relative position adjustment portion 26 are respectively provided at positions corresponding to corner portions 27b of the cutout portion 27 in the plane of the operation panel portion 22. In other words, the X-ray irradiation range adjustment portion 25 and the relative position adjustment portion 26 are respectively provided at positions opposite to the side of the open end portion 27a of the cutout portion 27 to which the gripping portion 3 is provided in the plane of the operation panel portion 22.

Further, as shown in FIG. 5, the X-ray irradiation range adjustment portion 25 and the relative position adjustment portion 26 are respectively provided on both sides of the gripping portion 3 in the direction (X-direction) in which gripping portion 3 extends in the operation panel portion 22 centering on the gripping portion 3. Specifically, the plurality of operation input portions 24 is arranged in the first arrangement region 10 and the second arrangement region 11 of the panel portion 22a. That is, as shown in FIG. 5, the X-ray irradiation range adjustment portion 25 and the relative position adjustment portion 26 are respectively provided in symmetrical positions with respect to the gripping portion 3 centering on the gripping portion 3 in the operation panel portion 22.

Figure 6:
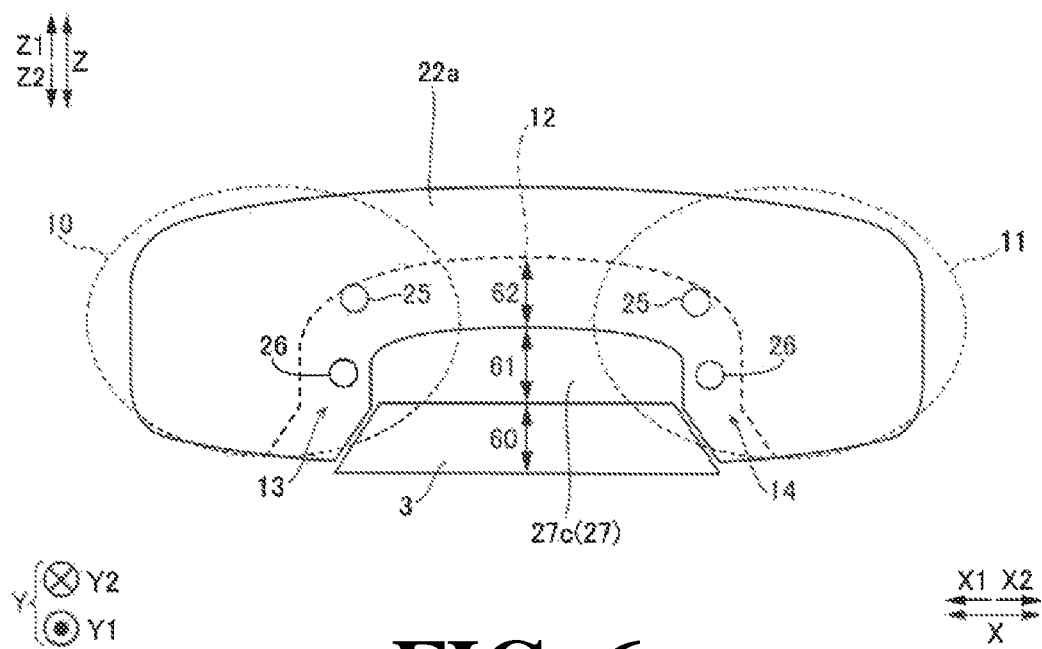
FIG. 6 is a schematic diagram for explaining a region in which an X-ray irradiation range adjustment portion and a relative position adjustment portion are arranged according to one embodiment.

As shown in FIG. 6, the X-ray irradiation range adjustment portion 25 and the relative position adjustment portion 26 are arranged in the region 13 where the first arrangement region 10 and the third arrangement region 12 overlap and in the region 14 where the second arrangement region 11 and the third arrangement region 12 overlap. Note that the third arrangement region 12 denotes a region in which the distance 62 from the inner surface 220 of the cutout portion 27 is substantially equal to the size 60 of the gripping portion 3 in the Z-direction among a region along the cutout portion 27 of the panel portion 22a.

Figure 7:
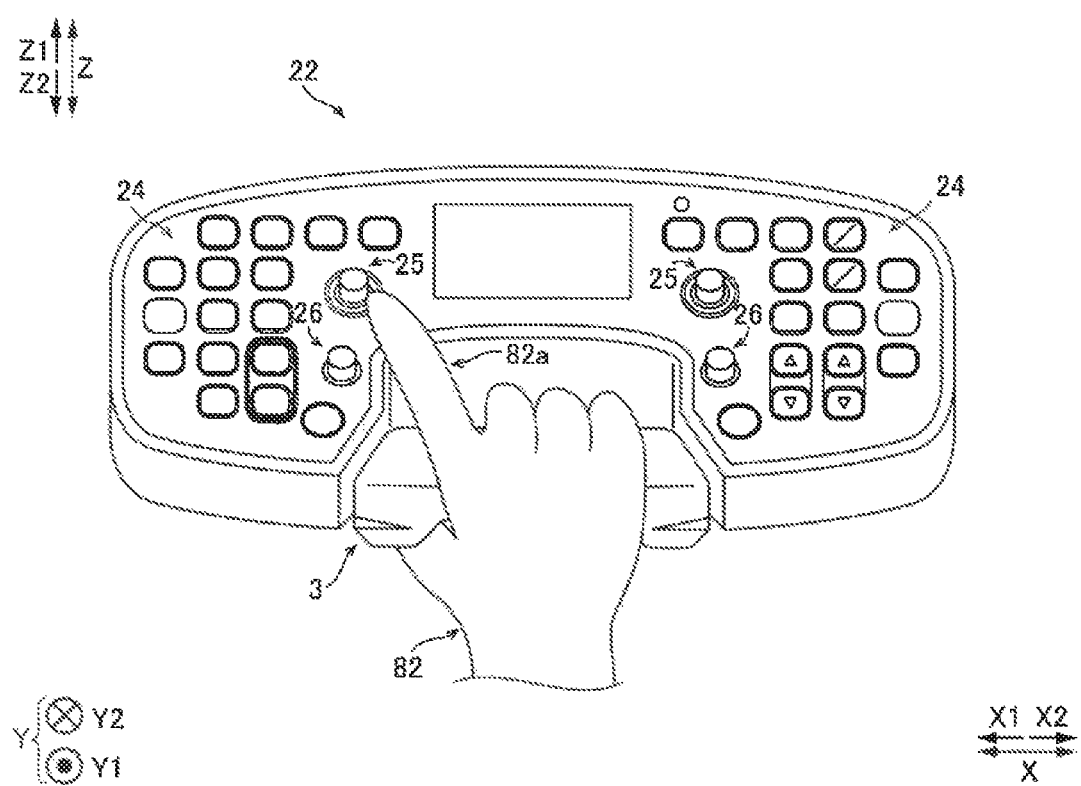
FIG. 7 is a schematic diagram showing a state in which an operator grips a gripping portion of an X-ray fluoroscopic imaging apparatus according to one embodiment.

Further, as shown in FIG. 6, it is sufficient to configure such that the Z-direction size 61 of the region 27c of the cutout portion 27 located on the side opposite to the open end portion 27a is a size that the operator 81 can grip the gripping portion 3. Specifically, it is sufficient to configure such that the Z-direction size 61 of the region 27c located on the side opposite to the open end portion 27a is substantially equal to the Z-direction size of the main body portion 3a of the gripping portion 3. By configuring such that the Z-direction size 61 of the region 27c is substantially equal to the Z-direction size of the main body portion 3a of the gripping portion 3, as shown in FIG. 7, the operation panel portion 22 is configured such that the X-ray irradiation range adjustment portion 25 and the relative position adjustment portion 26 can be manipulated by the forefinger 82a of the operator 81 in a state in which the operator 81 grips the gripping portion 3 with the hand 82.

(X-Ray Irradiation Range Adjustment Portion and Relative Position Adjustment Portion)

Figure 8:
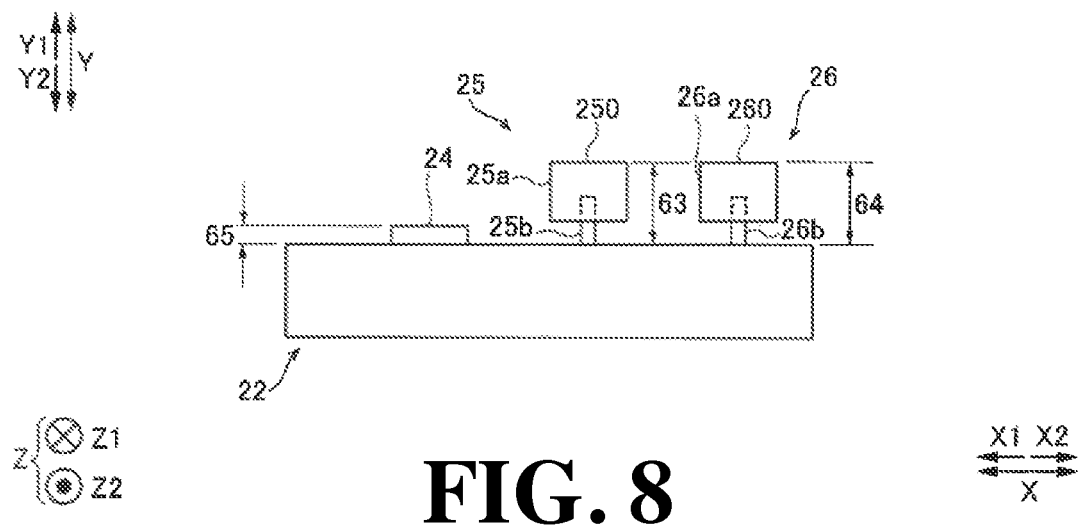
FIG. 8 is a schematic diagram for explaining the difference in size in a protrusion direction from a surface of an operation panel portion between an X-ray irradiation range adjustment portion and a relative position adjustment portion and other operation input portions according to one embodiment.

Next, with reference to FIG. 8 and FIG. 9, the configurations of the X-ray irradiation range adjustment portion 25 and the relative position adjustment portion 26 will be described. FIG. 8 is a schematic diagram of the operation panel portion 22 as viewed in the Z-direction. As shown in FIG. 8, the X-ray irradiation range adjustment portion 25 and the relative position adjustment portion 26 are each configured to be larger in size than other operation input portion 24 in a direction of protruding from a surface of the operation panel portion 22. Specifically, it is configured such that the height 64 of the X-ray irradiation range adjustment portion 25 in the direction projecting from the surface of the operation panel portion 22 and the height 65 of the relative positon adjustment portion 26 in the direction of protruding from the surface of the operation panel portion 22 are each larger than the height 63 of other operation panel portions 24 in the direction of protruding from the surface of the operation panel portion 22.

The height 64 of the X-ray irradiation range adjustment portion 25 in the direction of projecting from the surface of the operation panel portion 22 and the height 65 of the relative position adjustment portion 26 in the direction of projecting from the surface of the operation panel portion 22 are preferably larger than the heights of other operation input portions 24 so as to be able to access the X-ray irradiation range adjustment portion 25 or the relative position adjustment portion 26 when the finger 82a is extended toward the X-ray irradiation range adjustment portion 25 or the relative position adjustment portion 26 in a state in which the operator 81 grips the gripping portion 3. In the example shown in FIG. 8, for convenience of explanation, the X-ray irradiation range adjustment portion 25 and the relative position adjustment portion 26 are illustrated as aligned in the X-direction.

As shown in FIG. 8, the X-ray irradiation range adjustment portion 25 is provided with a placement portion 25a on which the finger 82a of the operator 81 is placed and a shaft portion 25b. On the surface of the placement portion 25a, a placement surface 25c on which the finger 82a of the operator 81 is placed is provided. Further, a shaft portion 25b is provided on the opposite side of the placement surface 25c in the placement portion 25a. One side of the shaft portion 25b is connected to the placement portion 25a, and the other side thereof is connected to the panel portion 22a. Further, the relative position adjustment portion 26 is also provided with a placement portion 26a on which the finger 82a of the operator 81 is placed and a shaft portion 26b. Similarly to the placement portion 25a, the placement portion 26a is also provided with a placement surface 26c on which the finger 82a of the operator 81 is placed. The configuration of the relative position adjustment portion 26 is the same as the configuration of the X-ray irradiation range adjustment portion 25, so the detailed description will be omitted. The X-ray irradiation range adjustment portion 25 and the relative position adjustment portion 26 are each a so-called joystick.

Figure 9:
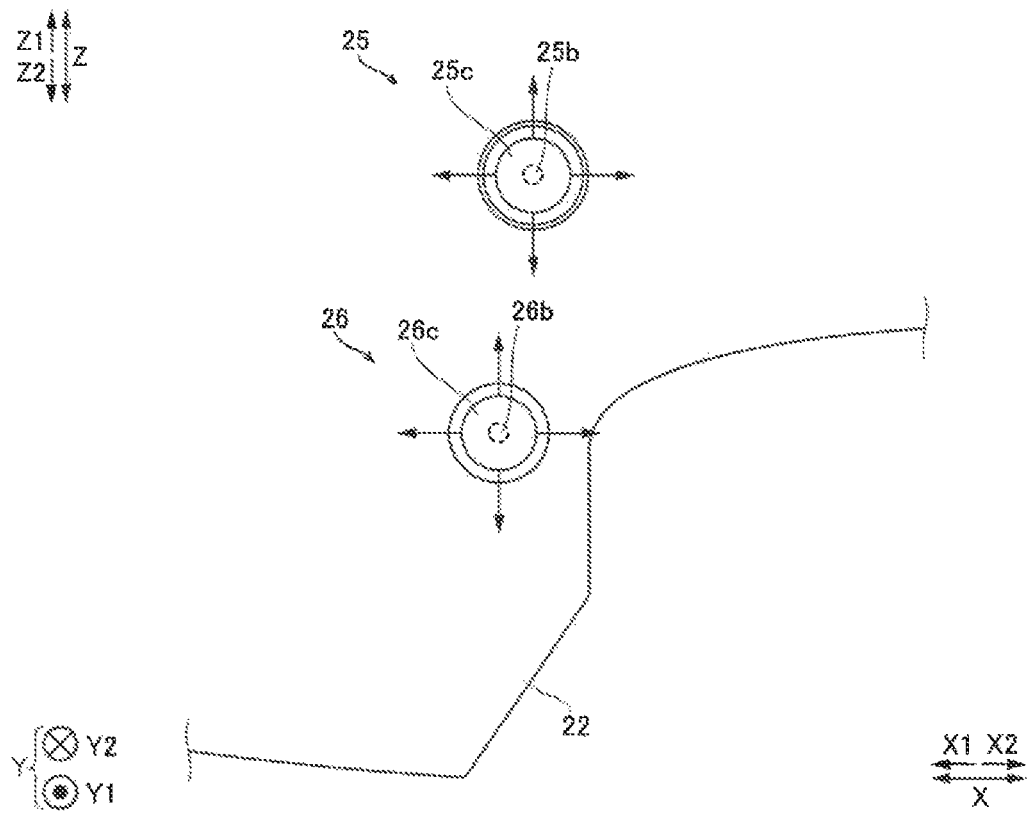
FIG. 9 is a schematic diagram for explaining a movement direction of an X-ray irradiation range adjustment portion and a relative position adjustment portion according to one embodiment.

FIG. 9 is an enlarged schematic diagram showing a portion in which the X-ray irradiation range adjustment portion 25 and the relative position adjustment portion 26 in the operation panel portion 22 are arranged. As shown in FIG. 9, the X-ray irradiation range adjustment portion 25 is configured to be movable in the radial direction centering on the shaft portion 25b in a state in which the operator 81 is placing the finger 82a on the placement portion 25a (placement surface 25c). Further, the relative position adjustment portion 26 is also configured to be movable in the radial direction centering on the shaft portion 26b in a state in which the operator 81 places the finger 82a on the placement portion 26a (placement surface 26c).

In this embodiment, the X-ray irradiation range adjustment portion 25 is configured to be movable in the up, down, left, and right directions of the radial direction centering on the shaft portion 25b. Further, the relative position adjustment portion 26 is also configured to be movable in the up, down, left, and right directions in the radial direction centering on the shaft portion 26b similar to the X-ray irradiation range adjustment portion 25. Note that the movement in the radial direction centering on the shaft portion 25b (shaft portion 2 includes the meaning of the movement of the placement portion 25a (placement portion 26a) in the radial direction by tilting the shaft portion 25b (shaft portion 2 in the radial direction and the movement of the placement portion 25a (placement portion 26a) in the radial direction together with the shaft portion 25b (shaft portion 2 without tilting the shaft portion 25b (shaft portion 2. Note that the X-ray irradiation range adjustment portion 25 and the relative position adjustment portion 26 may be configured to be movable in all directions of the radial direction.

The X-ray irradiation range adjustment portion 25 and the relative position adjustment portion 26 are configured to accept an input for adjusting the X-ray irradiation range 70 and an input for adjusting the relative position of the top board 1 and the imaging system 2 based on the movement direction of the shaft portion 25b and the shaft portion 26b, respectively. The details of the adjustment of the X-ray irradiation range 70 by the X-ray irradiation range adjustment portion 25 and the adjustment of the relative position of the top board 1 and the imaging system 2 by the relative position adjustment portion 26 will be described later.

In this embodiment, the other operation input portions 24 are each configured by a push-down button, and is configured to be able to receive an input to each operation input portion 24 by being pressed down by the operator 81. Further, the X-ray irradiation range adjustment portion 25 and the relative position adjustment portion 26 are each configured to be able to receive a predetermined input by being pushed in the direction toward the panel portion 22a. (Adjustment of the X-Ray Irradiation Range)

Next, the adjustment of the X-ray irradiation range 70 will be described with reference to FIG. 10. The collimator 23 is adjusted when the operator 81 operates the X-ray irradiation range adjustment portion 25. In other words, the X-ray irradiation range 70 is adjusted in accordance with the adjustment of the collimator 23 by the operator 81.

Figure 10:
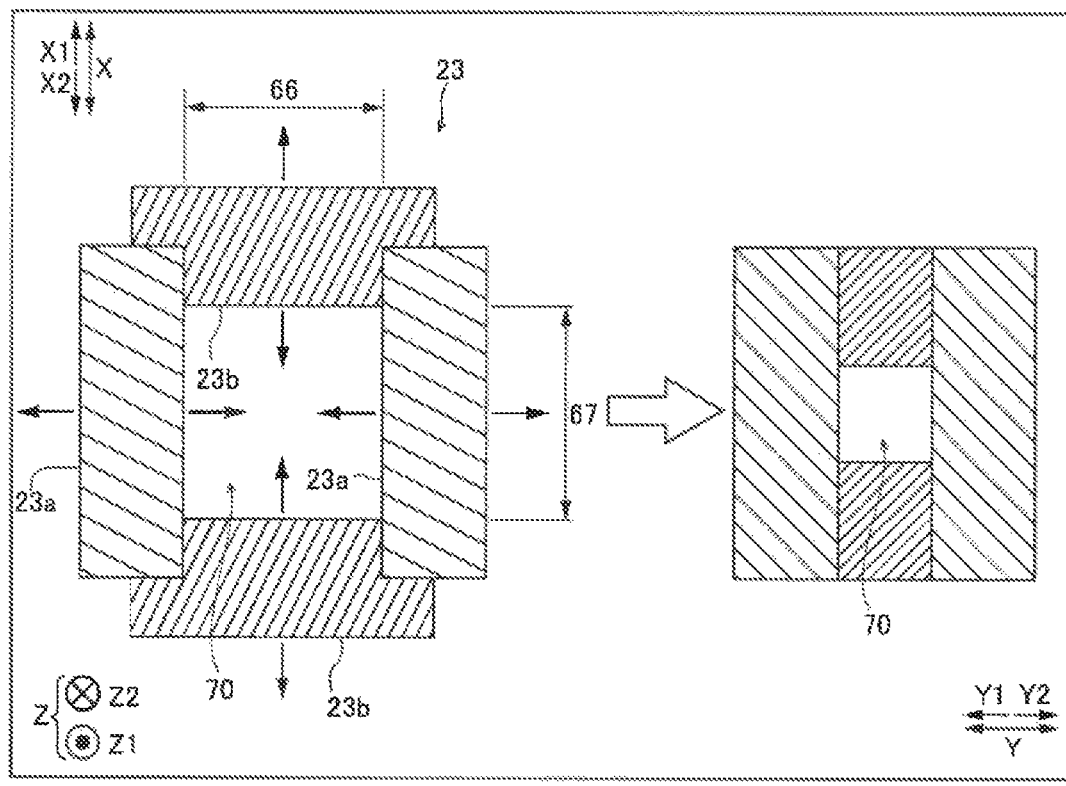
FIG. 10 is a schematic diagram for explaining an adjustment of an X-ray irradiation range by an X-ray irradiation range adjustment portion according to one embodiment.

As shown in FIG. 10, the collimator 23 includes a pair of first leaf portions 23a arranged in the Y-direction and a pair of second leaf portions 23b arranged in the X-direction. The collimator 23 is configured to be able to adjust the X-ray irradiation range 70 by moving the first leaf portion 23a and the second leaf portion 23b based on the input of the X-ray irradiation range adjustment portion 25. Specifically, the collimator 23 is configured to be able to adjust the X-ray irradiation range 70 by moving the first leaf portion 23a in the Y-direction and the second leaf portion 23b in the X-direction based on the input of the X-ray irradiation range adjustment portion 25.

The first leaf portion 23a is configured to be movable in the Y-direction based on the input caused by the movement of the X-ray irradiation range adjustment portion 25 by the operator 81 in the left-right direction in the plane of the operation panel portion 22. Specifically, the first leaf portion 23a is configured to move so as to decrease the distance 66 between the first leaf portions 23a when there is an input in the right direction. Further, the first leaf portion 23a is configured to move so as to increase the distance 66 between the first leaf portions 23a when there is an input in the left direction. Note that the direction of moving the first leaf portion 23a may be reversed in the left-right direction. That is, it may be configured such that the input in the right direction causes the movement of the first leaf portion 23a so that the distance 66 between the first leaf portions 23a increases and that the input in the left direction causes the movement of the first leaf portion 23a so that the distance 66 between the first leaf portions 23a decreases.

The second leaf portion 23b is configured to be movable based on the input from the X-ray irradiation range adjustment portion 25. Specifically, the second leaf portion 23b is configured to be movable in the X-direction based on the movement of the X-ray irradiation range adjustment portion 25 in the up-down direction in the plane of the operation panel portion 22. When there is an input in the upward direction from the X-ray irradiation range adjustment portion 25, the second leaf portion 23b is configured to move so as to decrease the distance 67 between the second leaf portions 23b. When there is an input in the downward direction from the X-ray irradiation range adjustment portion 25, the second leaf portion 23b is configured to move so as to increase the distance 67 between the second leaf portions 23b. That is, when the operator 81 moves the X-ray irradiation range adjustment portion 25 in the up-down direction and in left-right direction in the plane of the operation panel portion 22, the first leaf portion 23a and the second leaf portion 23b are moved, so that the X-ray irradiation range 70 can be adjusted.

Note that the direction of moving the second leaf portion 23b may be reversed in the up-down direction. That is, it may be configured such that the input in the upward direction causes the movement of the second leaf portion 23b so that the distance 67 between the second leaf portions 23b increases and that the input in the downward direction causes the movement of the second leaf portions 23b so that distance 67 between the second leaf portions 23b decreases. (Adjustment of the Relative Position of the Top Board)

Figure 11:
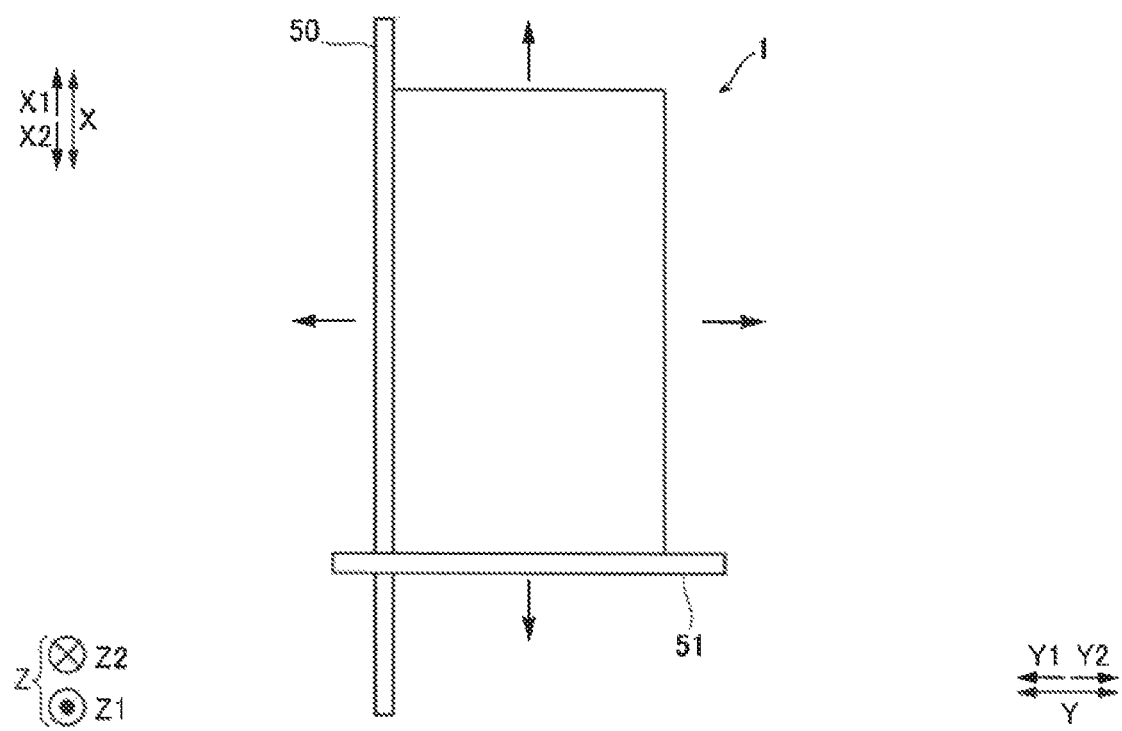
FIG. 11 is a schematic diagram for explaining an adjustment of a relative position of a top board by a relative position adjustment portion according to one embodiment.

Next, the adjustment of the relative position of the top board 1 in the relative position adjustment portion 26 will be described with reference to FIG. 11. The top board moving mechanism 5 moves the top board 1 based on the input by the relative position adjustment portion 26. Specifically, the top board moving mechanism 5 moves the top board 1 based on the movement direction of the relative position adjustment portion 26 in the plane of the operation panel portion 22. That is, the top board moving mechanism 5 moves the top board 1 in the X1-direction when the relative position adjustment portion 26 is moved upward in the plane of operation panel portion 22.

Further, the top board moving mechanism 5 moves the top board 1 in the X2-direction when the relative position adjustment portion 26 is moved in the downward direction in the plane of operation panel portion 22. Further, the top board moving mechanism 5 moves the top board 1 in the Y2-direction when the relative position adjustment portion 26 is moved in the right direction in the plane of operation panel portion 22. Further, the top board moving mechanism 5 moves the top board 1 in the Y1-direction when the relative position adjustment portion 26 is moved in the left direction in the plane of operation panel portion 22. Therefore, the operator 81 can move the top board 1 to an arbitrary position by moving the relative position adjustment portion 26 in the direction in which the top board 1 is to be moved.

(Effects of this Embodiment)

In this embodiment, the following effects can be obtained.

In this embodiment, as mentioned above, the X-ray fluoroscopic imaging apparatus 100 is provided with the top board 1 on which the subject 80 is placed, the imaging system 2 including the X-ray source 20 for emitting X-rays toward the subject 80 and a detector 21 for detecting X-rays emitted from the X-ray source 20 and transmitted through the subject 80, and the operation panel portion 22 provided integrally with the gripping portion 3 gripped by the operator 81 when moving the imaging system 2 and a plurality of operation input portions 24 provided integrally with the imaging system 2 and configured to receive operation inputs for operating the imaging system 2. The gripping portion 3 extends along the direction substantially parallel to the operation panel portion 22 and is connected to the operation panel portion 22, and the plurality of operation input portions 24 includes at least the X-ray irradiation range adjustment portion 25 for adjusting the X-ray irradiation range 70. The X-ray irradiation range adjustment portion 25 is provided at the position on the side of the gripping portion 3 in the plane of the operation panel portion 22. This makes it possible to arrange the X-ray irradiation range adjustment portion 25 close to the gripping portion 3, so that it is possible to operate the X-ray irradiation range adjustment portion 25 in a state in which the operator 81 grips the gripping portion 3. As a result, it is possible to efficiently adjust the X-ray irradiation range 70 in a state in which the operator 81 grips the gripping portion 3.

Further, in this embodiment, as described above, the plurality of operation input portions 24 further include the relative position adjustment portion 26 for receiving the input for adjusting the relative position of the top board 1 and the imaging system 2. Not only the X-ray irradiation range adjustment portion 25 but also the relative position adjustment portion 26 are provided at positions on the side of the gripping portion 3 in the plane of the operation panel portion 22. With this, it is possible to perform not only the adjustment of the X-ray irradiation range 70 but also the adjustment of the relative position of the top board 1 and the imaging system 2 in a state in which the gripping portion 3 is gripped. As a result, the adjustment of the X-ray irradiation range 70 and the adjustment of the relative position of the top board 1 and the imaging system 2 can be efficiently performed without visually recognizing the operation panel portion 22.

Further, in this embodiment, as described above, the plurality of operation input portions 24 are arranged in a plurality of rows in the direction intersecting with the gripping portion 3 in the plane of the operation panel portion 22. Further, the X-ray irradiation range adjustment portion 25 and the relative position adjustment portion 26 are arranged in the row 30*d* closest to the side of the gripping portion 3 among the plurality of rows 30 in which the plurality of operation input portions 24 is arranged. With this, the X-ray irradiation range adjustment portion 25 and the relative position adjustment portion 26 can be arranged at positions closer to the gripping portion 3 than other operation input portions 24. As a result, the X-ray irradiation range adjustment portion 25 and the relative position adjustment portion 26 can be easily operated in a state in which the gripping portion 3 is gripped. Therefore, the adjustment of the X-ray irradiation range 70 and the adjustment of the relative position of the top board 1 and the imaging system 2 can be performed more efficiently.

Further, in this embodiment, as described above, the row 30*d* in which the X-ray irradiation range adjustment portion 25 and the relative position adjustment portion 26 are arranged is a row 30*d* located at a position closest to the connecting portion 3*b* of the gripping portion 3 among the plurality of rows 30 in which the plurality of operation input portions 24 is arranged in the plane of the operation panel portion 22. With this, the X-ray irradiation range adjustment portion 25 and the relative position adjustment portion 26 can be arranged at positions closer to the gripping portion 3 than the other operation input portions 24. As a result, the X-ray irradiation range adjustment portion 25 and the relative position adjustment portion 26 can be more easily operated in a state in which the gripping portion 3 is gripped. Therefore, the adjustment of the X-ray irradiation range 70 and the adjustment of the relative position of the top board 1 and the imaging system 2 can be performed further more efficiently.

Further, in this embodiment, as described above, the operation panel portion 22 is provided with the cutout portion 27 and the gripping portion 3 is provided to connect the opposing inner surfaces of the cutout portion 27 on the side of the open end portion of the cutout portion 27 with each other. The X-ray irradiation range adjustment portion 25 and the relative position adjustment portion 26 are respectively provided at positions corresponding to corner portions 27*b* of the cutout portion 27 in the plane of the operation panel portion 22. With this, unlike the configuration in which a U-shaped gripping portion 3 is attached to the side surface of the operation panel portion 22 that does not have a cutout portion 27, it is possible to prevent the gripping portion 3 from protruding from the side surface of the operation panel portion 22. As a result, it is possible to prevent other devices or the operator 81 from colliding with the gripping portion 3.

Further, in comparison with the configuration in which the X-ray irradiation range adjustment portion 25 and the relative position adjustment portion 26 are provided on the side of the open end portion of the cutout portion 27, the gripping portion 3, the X-ray irradiation range adjustment portion 25, and the relative position adjustment portion 26 can be arranged at positions apart from each other to some extent. Therefore, in a state in which the user grips the gripping portion 3, it is possible to arrange the X-ray irradiation range adjustment portion 25 and the relative position adjustment portion 26 at positions (distance) which can be easily operated by a forefinger 82*a* (second finger) which is the most dexterous finger among human fingers. As a result, the X-ray irradiation range adjustment portion 25 and the relative position adjustment portion 26 can be arranged at positions which are close to the gripping portion 3 and easily operable with a forefinger 82*a*.

Further, in this embodiment, as described above, the operation panel portion 22 is provided with the cutout portion 27 and the gripping portion 3 is provided to connect the opposing inner surfaces of the cutout portion 27 on the side of the open end portion of the cutout portion 27 with each other. The X-ray irradiation range adjustment portion 25 and the relative position adjustment portion 26 are respectively provided at positions opposite to the side of the open end portion 27a of the cutout portion 27 to which the gripping portion 3 is provided in the plane of the operation panel portion 22. Even by configuring as described above, in the same manner as the configuration in which the X-ray irradiation range adjustment portion 25 and the relative position adjustment portion 26 are respectively provided at positions corresponding to the corner portions 27b of the cutout portion 27 in the plane of the operation panel portion 22, the X-ray irradiation range adjustment portion 25 and the relative position adjustment portion 26 can be arranged at positions which are close to the gripping portion 3 and easily operable with an forefinger 82a.

Further, in this embodiment, as described above, the X-ray irradiation range adjustment portion 25 and the relative position adjustment portion 26 are each configured to be larger in size than other operation input portions 24 in a direction of protruding from a surface of the operation panel portion 22. With this, since the X-ray irradiation range adjustment portion 25 and the relative position adjustment portion 26 protrude from the surface of the operation panel portion 22, it is possible to access the X-ray irradiation range adjustment portion 25 and the relative position adjustment portion 26 naturally without visually recognizing them by simply moving a finger 82a above the surface of the operation panel portion 22. Therefore, the X-ray irradiation range 70 and the relative position of the top board 1 can be adjusted without visually recognizing the operation panel portion 22. As a result, the operability at the time of adjusting the X-ray irradiation range 70 and the relative position of the top board 1 can be further improved.

Further, in this embodiment, as described above, the X-ray irradiation range adjustment portion 25 and the relative position adjustment portion 26 respectively are configured as follows. The X-ray irradiation range adjustment portion 25 and the relative position adjustment portion 26 are respectively provided with a placement portion (the placement portion 25a, the placement portion 26a) on which the finger 82a of the operator 81 is placed and a shaft portion (the shaft portion 25b, the shaft portion 26b). The X-ray irradiation range adjustment portion 25 and the relative position adjustment portion 26 are respectively movable in the radial direction centering on the shaft portion (the shaft portion 25b, the shaft portion 26b) in a state in which the operator 81 is placing the finger 82a on the placement portion (the placement portion 25a, the placement portion 26a). The X-ray irradiation range adjustment portion 25 and the relative position adjustment portion 26 respectively receive an input for adjusting the X-ray irradiation range 70 and an input for adjusting the relative position of the top board 1 and the imaging system 2 based on the movement direction of the shaft portion (the shaft portion 25b, the shaft portion 26b).

Thus, in a state in which the finger 82a is placed on the placement portion (the placement portion 25a, the placement portion 26a), by moving the center of gravity of the placement portion (the placement portion 25a, the placement portion 26a), the X-ray irradiation range adjustment portion 25 and the relative position adjustment portion 26 can be moved. Therefore, as compared with the configuration in which the adjustment of the X-ray irradiation range 70 and the adjustment of the relative position of the top board 1 are performed using input portions corresponding to each direction, such as, e.g., arrow keys, it is possible to intuitively operate the X-ray irradiation range adjustment portion 25 and the relative position adjustment portion 26. As a result, even in the case of operating the X-ray irradiation range adjustment portion 25 and the relative position adjustment portion 26 without visually recognizing the operation panel portion 22, it is possible to easily adjust the X-ray irradiation range 70 and the relative position of the top board 1.

Further, in this embodiment, as described above, the X-ray irradiation range adjustment portion 25 and the relative position adjustment portion 26 are respectively provided on both sides of the gripping portion 3 in the direction in which gripping portion 3 extends in the operation panel portion 22 centering on the gripping portion 3. With this configuration, since the X-ray irradiation range adjustment portion 25 and the relative position adjustment portion 26 are provided on both sides in the extending direction of the gripping portion 3 centering on the gripping portion 3, even if the user grips the gripping portion 3 with either hand, in a state in which the gripping portion 3 is gripped, it is possible to manipulate the X-ray irradiation range adjustment portion 25 and the relative position adjustment portion 26. Therefore, as compared with the configuration in which the X-ray irradiation range adjustment portion 25 and the relative position adjustment portion 26 are provided on only one side of the operation panel portion 22, the operability of the X-ray irradiation range adjustment portion 25 and the relative position adjustment portion 26 can be improved. As a result, the usability can be improved.

Modified Embodiment

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the above embodiment, an example is shown in which the operation input portion 24 is configured to include the X-ray irradiation range adjustment portion 25 and the relative position adjustment portion 26, but the present invention is not limited to this. As long as it includes the X-ray irradiation range adjustment portion 25, the operation input portion 24 may not include the relative position adjustment portion 26. However, it is difficult to finely adjust the imaging position only by moving the imaging system 2 with the gripping portion 3, the operation input portion 24 preferably includes the relative position adjustment portion 26.

Note that in cases where the plurality of operation input portions 24 includes the relative position adjustment portion 26, the relative position adjustment portion 26 may be arranged at any position. However, in order to improve the operability, it is preferable that the relative position adjustment portion 26 be arranged at an operable position in a state in which the operator 81 grips the gripping portion 3.

In the above embodiment, an example is shown in which it is configured such that the plurality of operation input portions 24 is arranged in a plurality of rows 30 and that the X-ray irradiation range adjustment portion 25 and the relative position adjustment portion 26 are arranged in the row 30d closest on the side of the gripping portion 3, but the present invention is not limited to this. As long as the X-ray irradiation range adjustment portion 25 is arranged at an operable position in a state in which the operator 81 grips the gripping portion 3, any other operation input portions 24 may be arranged in any way. However, if other operation input portions 24 are arranged between the X-ray irradiation range adjustment portion 25 and the gripping portion 3, the distance between the gripping portion 3 and the X-ray irradiation range adjustment portion 25 increases, so that the operability of the X-ray irradiation range adjustment portion 25 by the operator 81 deteriorates. Therefore, it is preferable that no other operation input portions 24 be arranged between the X-ray irradiation range adjustment portion 25 and the gripping portion 3.

Further, in the aforementioned embodiment, an example is shown in which it is configured such that the row 30d in which the X-ray irradiation range adjustment portion 25 and the relative position adjustment portion 26 are arranged is arranged at the position closest to the connecting portion 3b of the gripping portion 3, but the present invention is not limited to this. Depending on the position of the connecting portion 3b of the gripping portion 3, the row 30d in which the X-ray irradiation range adjustment portion 25 is arranged may not be the row arranged at the position closest to the connecting portion 3b. As long as the X-ray irradiation range adjustment portion 25 is arranged at an operable position in a state in which the operator 81 grips the gripping portion 3, the X-ray irradiation range adjustment portion 25 may not be arranged in the row 30d arranged at the position closest to the connecting portion 3b.

Further note that in the above embodiment, an example is shown in which it is configured such that the operation panel portion 22 is provided with the cutout portion 27, but the present invention is not limited to this. It may be configured such that the operation panel portion 22 is not provided with the cutout portion 27. In cases where the operation panel portion 22 is not provided with the cutout portion 27, a U-shaped gripping portion 3 may be attached to the operation panel portion 22. However, when the U-shaped gripping portion 3 is attached to the operation panel portion 22, it is preferable that the operation panel portion 22 is provided with the cutout portion 27 because the gripping portion 3 protrudes from the operation panel portion 22.

Moreover, in the above embodiment, an example is shown in which it is configured such that the gripping portion 3 is provided so as to mutually connect the opposing inner surfaces of the cutout portion 27 on the side of the open end portion 27a of the cutout portion 27, but the present invention is not limited to this. As long as the X-ray irradiation range adjustment portion 25 can be operated with the operator 81 gripping the gripping portion 3, the gripping portion 3 may be provided at any position.

In the above embodiment, an example is shown in which it is configures such that the X-ray irradiation range adjustment portion 25 and the relative position adjustment portion 26 are provided at positions corresponding to the corner portions 27b of the cutout portion 27, but the present invention is limited to this. As long as the X-ray irradiation range adjustment portion 25 can be operated in a state in which the operator 81 grips the gripping portion 3, the X-ray irradiation range adjustment portion 25 may be disposed at any position other than the position corresponding to the corner portion 27b of the cutout portion 27.

In the above embodiment, an example is shown in which it is configured such that the X-ray irradiation range adjustment portion 25 and the relative position adjustment portion 26 are provided at positions opposite to the side of the open end portion 27a of the cutout portion 27 provided with the gripping portion 3, but the present invention is not limited to this. As long as the X-ray irradiation range adjustment portion 25 can be operated in a state in which the operator 81 grips the gripping portion 3, the X-ray irradiation range adjustment portion 25 may be arranged at any position other than the position opposite to the side of the open end portion 27a of the cutout portion 27.

Further, in the aforementioned embodiment, an example is shown in which it is configured such that the height 64 of the X-ray irradiation range adjustment portion 25 in the direction projecting from the surface of the operation panel portion 22 and the height 65 of the relative position adjustment portion 26 in the direction of protruding from the surface of the operation panel portion 22 are each larger than the height 63 of other operation panel portions 24 in the direction of protruding from the surface of the operation panel portion 22, but the present invention is not limited to this. It may be configured such that the height 64 of the X-ray irradiation range adjustment portion 25 in the direction projecting from the surface of the operation panel portion 22 and the height 65 of the relative position adjustment portion 26 in the direction of protruding from the surface of the operation panel portion 22 are equal to the height 63 of other operation panel portions 24 in the direction of protruding from the surface of the operation panel portion 22.

However, if the height 64 of the X-ray irradiation range adjustment portion 25 in the direction projecting from the surface of the operation panel portion 22 and the height 65 of the relative position adjustment portion 26 in the direction of protruding from the surface of the operation panel portion 22 are equal to the height 63 of other operation input portions 24 in the direction of protruding from the surface of the operation panel portion 22, the X-ray irradiation range adjustment portion 25 and the other operation input portion 24 cannot be distinguished, so it becomes difficult for the operator 81 to operate without visually recognizing the operation panel portion 22, which deteriorates the operability. For this reason, it is preferable that the height 64 of the X-ray irradiation range adjustment portion 25 in the direction projecting from the surface of the operation panel portion 22 and the height 65 of the relative position adjustment portion 26 in the direction of protruding from the surface of the operation panel portion 22 be each larger than the height 63 of other operation input portions 24 in the direction of protruding from the surface of the operation panel portion 22.

In the above embodiment, an example is shown in which it is configured such that the X-ray irradiation range adjustment portion 25 and the relative position adjustment portion 26 are provided with the placement portion (the placement portion 25a, the placement portion 26a) on which the finger 82a of the operator 81 is placed and the shaft portion (the shaft portion 25b, the shaft portion 26b), but the present invention is not limited to this. For example, the X-ray irradiation range adjustment portion 25 and the relative position adjustment portion 26 may be push-in buttons like other operation input portions 24.

However, in cases where the X-ray irradiation range adjustment portion 25 and the relative position adjustment portion 26 are respectively configured by push-in buttons, it is necessary to provide buttons each corresponding to each direction. In cases where the X-ray irradiation range adjustment portion 25 and the relative position adjustment portion 26 each include a button corresponding to each direction, the operator 81 has to move the finger 82a to each button, which may cause an erroneous operation. Therefore, it is preferable that the X-ray irradiation range adjustment portion 25 and the relative position adjustment portion 26 each have a placement portion (the placement portion 25a, the placement portion 26a) and a shaft portion (the shaft portion 25b, the shaft portion 26b).

Also, in the above embodiment, an example is shown in which it is configured such that the X-ray irradiation range adjustment portion 25 and the relative position adjustment portion 26 are provided on both sides in the direction (X-direction) in which the gripping portion 3 extends, centering on the gripping portion 3, but the present invention is not limited to this. The X-ray irradiation range adjustment portion 25 and the relative position adjustment portion 26 may be provided on either side in the direction (X-direction) in which the gripping portion 3 extends, centering on the gripping portion 3.

However, in cases where the X-ray irradiation range adjustment portion 25 and the relative position adjustment portion 26 are provided on either side in the direction (X-direction) in which the gripping portion 3 extends, centering on the gripping portion 3, depending on which hand the operator 81 grips the gripping portion 3, the X-ray irradiation range adjustment portion 25 and the relative position adjustment portion 26 may be difficult to operate. For this reason, the X-ray irradiation range adjustment portion 25 and the relative position adjustment portion 26 may be provided on either side in the direction (X-direction) in which the gripping portion 3 extends, centering on the gripping portion 3.

In the above embodiment, an example is shown in which the X-ray source 20 is provided to the base portion 44 via the holding portion 47a and the connecting portion 47b is moved together with the base portion 44 in the X-direction and the Y-direction, but the present invention is not limited to this. For example, it may be configured to further include X-ray source moving mechanism capable of moving the X-ray source 20 so that the X-ray source 20 is moved by the X-ray source moving mechanism according to the movement of the imaging system 2.

In the above embodiment, an example is shown in which the X-ray irradiation range adjustment portion 25 and the relative position adjustment portion 26 have substantially the same shape, but the present invention is not limited thereto. It may be configures such that the shape of the X-ray irradiation range adjustment portion 25 and the shape of the relative position adjustment portion 26 may be different from each other.

In the above embodiment, an example is shown in which the detector 21 is provided on the Z1-direction side and the X-ray source 20 is provided on the Z2-direction side, but the present invention is not limited to this. It may be configured such that the X-ray source 20 is provided on the Z1-direction side and the detector 21 is provided on the Z2-direction side.

In the above embodiment, an example is shown in which it is configured such that the X-ray irradiation range adjustment portion 25 is provided above the relative position adjustment portion 26 in the plane of the operation panel portion 22, but the present invention is not limited to this. The X-ray irradiation range adjustment portion 25 may be provided below the relative position adjustment portion 26.

The invention claimed is:

1. An X-ray fluoroscopic imaging apparatus comprising:
a top board configured to place a subject thereon;
an imaging system including an X-ray source configured to emit X-rays toward the subject and a detector configured to detect X-rays emitted from the X-ray source and transmitted through the subject;
a gripping portion configured to be gripped by an operator when the operator moves the imaging system; and
an operation panel portion provided integrally to the imaging system, provided with a plurality of operation input devices each for receiving an operation input for operating the imaging system,
wherein the gripping portion extends along a direction substantially parallel to the operation panel portion, and is connected to the operation panel portion,
wherein the plurality of operation input devices includes at least X-ray irradiation range adjusters for adjusting an X-ray irradiation range, and
wherein the X-ray irradiation range adjusters include mechanical adjusters that are provided on both sides of the gripping portion in a direction in which the gripping portion extends at a position on a side of the gripping portion in a plane of the operation panel portion.

2. The X-ray fluoroscopic imaging apparatus as recited in claim 1,
wherein the plurality of operation input devices further includes a relative position adjuster configured to receive an input for adjusting a relative position of the top board and the imaging system, and
wherein not only the X-ray irradiation range adjusters but also the relative position adjuster are provided at positions on the side of the gripping portion in the plane of the operation panel portion.

3. The X-ray fluoroscopic imaging apparatus as recited in claim 2,
wherein the plurality of operation input devices is arranged in a plurality of rows in a direction intersecting with the gripping portion in the plane of the operation panel portion, and
wherein the X-ray irradiation range adjusters and the relative position adjuster are arranged in a row closest to the side of the gripping portion among the plurality of rows in which the plurality of operation input devices are arranged.

4. The X-ray fluoroscopic imaging apparatus as recited in claim 3,
wherein the row in which the X-ray irradiation range adjusters and the relative position adjuster are arranged is a row located at a position closest to a connecting portion of the gripping portion with respect to the operation panel portion among the plurality of rows in which the plurality of operation input devices is arranged in the plane of the operation panel portion.

5. The X-ray fluoroscopic imaging apparatus as recited in claim 3,
wherein the operation panel portion is provided with a cutout portion,
wherein the gripping portion is provided so as to connect opposing inner surfaces of the cutout portion on a side of an open end portion of the cutout portion, and
wherein the X-ray irradiation range adjusters and the relative position adjuster are respectively provided at positions corresponding to corner portions of the cutout portion in the plane of the operation panel portion.

6. The X-ray fluoroscopic imaging apparatus as recited in claim 3,
wherein the operation panel portion is provided with a cutout portion,
wherein the gripping portion is provided so as to connect opposing inner surfaces of the cutout portion on a side of an open end portion of the cutout portion, and
wherein the X-ray irradiation range adjusters and the relative position adjuster are respectively provided at positions opposite to the side of the open end portion of the cutout portion where the gripping portion is provided in the plane of the operation panel portion.

7. The X-ray fluoroscopic imaging apparatus as recited in claim 2,
wherein the X-ray irradiation range adjusters and the relative position adjuster are each configured to be larger in size than other operation input devices in a direction of protruding from a surface of the operation panel portion.

8. The X-ray fluoroscopic imaging apparatus as recited in claim 2,
wherein the X-ray irradiation range adjusters and the relative position adjuster are each provided with a placement portion on which a finger of the operator is placed and a shaft portion, and configured to be movable in a radial direction centering on the shaft portion in a state in which the finger is placed on the placement portion, and further configured to accept an input for adjusting the X-ray irradiation range and an input for adjusting the relative position of the top board and the imaging system, based on a movement direction of the shaft portion.

9. The X-ray fluoroscopic imaging apparatus as recited in claim 8,
wherein the operation panel portion includes a plurality of relative position adjusters that are respectively provided on both sides in the direction in which the gripping portion extends centering on the gripping portion in the operation panel portion.

* * * * *